(12) United States Patent
Nakao et al.

(10) Patent No.: US 11,957,557 B2
(45) Date of Patent: Apr. 16, 2024

(54) PANTS-TYPE DISPOSABLE DIAPER

(71) Applicant: KAO CORPORATION, Tokyo (JP)

(72) Inventors: Yuma Nakao, Utsunomiya (JP); Yuko Fukuda, Mouka (JP)

(73) Assignee: KAO CORPORATION, Tokyo (JP)

( * ) Notice: Subject to any disclaimer, the term of this patent is extended or adjusted under 35 U.S.C. 154(b) by 826 days.

(21) Appl. No.: 17/050,142

(22) PCT Filed: Apr. 5, 2019

(86) PCT No.: PCT/JP2019/015231
§ 371 (c)(1),
(2) Date: Oct. 23, 2020

(87) PCT Pub. No.: WO2019/208180
PCT Pub. Date: Oct. 31, 2019

(65) Prior Publication Data
US 2021/0093491 A1     Apr. 1, 2021

(30) Foreign Application Priority Data

Apr. 24, 2018   (JP) .................................. 2018-082802

(51) Int. Cl.
*A61F 13/15*      (2006.01)
*A61F 13/496*     (2006.01)
(Continued)

(52) U.S. Cl.
CPC ........ *A61F 13/5512* (2013.01); *A61F 13/496* (2013.01); *A61F 2013/15357* (2013.01);
(Continued)

(58) Field of Classification Search
CPC ................ A61F 13/5512; A61F 13/496; A61F 2013/15357; A61F 2013/15406; A61F 2013/5355
See application file for complete search history.

(56) References Cited

U.S. PATENT DOCUMENTS 5,807,371 A    9/1998 Toyoda et al.
8,152,787 B2   4/2012 Faulks et al.
(Continued)

FOREIGN PATENT DOCUMENTS

CN    103648463 A     3/2014
EP    0 752 239 A1    1/1997
(Continued)

OTHER PUBLICATIONS

U.S. Appl. No. 16/629,914, filed Jan. 9, 2020.
International Search Report, issued in PCT/JP2019/015231, PCT/ISA/210, dated Jun. 25, 2019.

*Primary Examiner* — Jacqueline F Stephens
(74) *Attorney, Agent, or Firm* — Birch, Stewart, Kolasch & Birch, LLP

(57) ABSTRACT

A diaper 1 has a disposal tape 10 on its outer surface. The disposal tape 10 is composed of a fixed portion 12, an extensible portion 15, and a fastening portion 18 arranged in that order along the longitudinal direction X1 of the disposal tape 10 and Z-folded in that order. Unfolded, the extensible portion 15 is extensible in the longitudinal direction X1 of the disposal tape 10. The disposal tape 10 in the unfolded configuration has a first connection region 31 where the extensible portion 15 and the fastening portion overlap and a second connection region 32 where the extensible portion 15 and the fixed portion 12 overlap. At least one of the first and second connection regions has a bonded region 33 and a non-bonded region 36 where the extensible portion 15 and the fastening portion 18 or fixed portion 12 are not bonded, the non-bonded region 36 being located longitudinally proximal to the bonded region 33.

14 Claims, 7 Drawing Sheets

(51) Int. Cl.
  *A61F 13/551* (2006.01)
  *A61F 13/535* (2006.01)
(52) U.S. Cl.
  CPC .............. *A61F 2013/15406* (2013.01); *A61F 2013/5355* (2013.01)

(56) References Cited

U.S. PATENT DOCUMENTS

| | | |
|---|---|---|
| 2003/0014030 A1 | 1/2003 | Andersson et al. |
| 2003/0124303 A1 | 7/2003 | Price et al. |
| 2014/0010984 A1 | 1/2014 | Bogaerts et al. |
| 2017/0281430 A1 | 10/2017 | Kurohara et al. |
| 2017/0312147 A1* | 11/2017 | Bianchi ............. A61F 13/53409 |
| 2017/0348167 A1 | 12/2017 | Tashiro et al. |
| 2018/0325749 A1 | 11/2018 | Yoshioka et al. |
| 2020/0030164 A1 | 1/2020 | Matsuda et al. |
| 2020/0237582 A1 | 7/2020 | Takahashi et al. |

FOREIGN PATENT DOCUMENTS

| | | |
|---|---|---|
| EP | 1 552 801 A1 | 7/2005 |
| EP | 1762207 A1 | 3/2007 |
| JP | 9-99010 A | 4/1997 |
| JP | 2001-46436 A | 2/2001 |
| JP | 2001-258938 A | 9/2001 |
| JP | 2003-235891 A | 8/2003 |
| JP | 2004-141841 A | 5/2004 |
| JP | 2004-298459 A | 10/2004 |
| JP | 2008-541924 A | 11/2008 |
| JP | 2009-507570 A | 2/2009 |
| JP | 2011-188970 A | 9/2011 |
| JP | 2012-75700 A | 4/2012 |
| JP | 2012-228423 A | 11/2012 |
| JP | 2013-121416 A | 6/2013 |
| JP | 2013-226382 A | 11/2013 |
| JP | 2013-248169 A | 12/2013 |
| JP | 2014-121409 A | 7/2014 |
| JP | 2014-233501 A | 12/2014 |
| JP | 2016-87912 A | 5/2016 |
| JP | 2016-112408 A | 6/2016 |
| JP | 6236569 B1 | 11/2017 |
| JP | 2018-121931 A | 8/2018 |
| JP | 2019-30634 A | 2/2019 |
| KR | 10-1796020 B1 | 11/2017 |
| RU | 2 302 848 C2 | 7/2007 |
| RU | 2 489 126 C2 | 8/2013 |
| WO | WO 2006/130053 A1 | 12/2006 |
| WO | WO 2007/032965 A1 | 3/2007 |
| WO | WO 2014/100187 A1 | 6/2014 |
| WO | WO 2017/081880 A1 | 5/2017 |
| WO | WO 2019/208178 A1 | 10/2019 |
| WO | WO 2019/208179 A1 | 10/2019 |
| WO | WO 2019/230317 A1 | 12/2019 |

* cited by examiner

PANTS-TYPE DISPOSABLE DISPOSABLE DIAPER

TECHNICAL FIELD

The present invention relates to a disposable pull-on diaper having a disposal tape.

BACKGROUND ART

Disposable diapers having a disposal tape are known. The disposable tape is to secure a used diaper in a rolled-up configuration for easy and hygienic disposal. Disposal tapes having an extensible portion have been proposed to provide ease of rolling up a diaper and securing the diaper in a rolled-up configuration. For example, patent literature 1 listed below discloses a laminate disposal tape tab comprising adjacent first and second tape tab elements and a plastically deformable extendible film having two end portions and an intermediate portion therebetween, one end portion being attached to the first face of the first tape tab element and the other end portion being attached to the first face of the second tape tab element. According to patent literature 1, a user can pinch one end of the disposal tape tab and extend the tab so that the tab becomes sufficiently stretched to be wrapped around the article.

A disposable diaper having a disposal tape in a Z-folded configuration is known, in which layers facing each other in a Z-fold configuration are releasably attached to each other. For instance, patent literature 2 below discloses a disposable diaper having a post-use tape composed of a lower layer, an upper layer, and an intermediate layer each formed of a tape base having one side thereof surface-treated for surface modifying. Each layer has a pressure-sensitive adhesive applied to one side thereof to provide an adhesive-coated side while leaving the other side non-coated. The three layers are connected in a first connection region and a second connection region and unfolded by separation at a first release region and a second release region.

CITATION LIST

Patent Literature

Patent literature 1: EP 1762207A1
Patent Literature 2: JP 2013-248169A

SUMMARY OF THE INVENTION

The present invention relates to a disposable pull-on diaper having a waist opening and a pair of leg openings and including a front portion adapted to be worn about the front of a wearer, a crotch portion adapted to be worn about the crotch of a wearer, and a rear portion adapted to be worn about the back of a wearer. The diaper has a disposal tape provided on its outer surface. The disposal tape includes a fixed portion that is fixed to the outer surface of the diaper, an extensible portion, and a fastening portion arranged in that order along the longitudinal direction of the disposal tape and Z-folded in that order. In the Z-folded configuration, the fastening portion and the extensible portion are releasably attached to each other, and the extensible portion and the fixed portion are also releasably attached to each other. In an unfolded linear configuration of the disposal tape, the extensible portion is extensible in the longitudinal direction of the disposal tape. The disposal tape in the unfolded linear configuration has a first connection region where the extensible portion and the fastening portion overlap and a second connection region where the extensible portion and the fixed portion overlap. Either one or both of the first and second connection region have a bonded region where the extensible portion and the overlapping fastening portion or fixed portion are bonded to each other and a non-bonded region where the extensible portion and the overlapping fastening portion or fixed portion are not bonded to each other, the non-bonded region being located longitudinally proximally to the bonded region.

BRIEF DESCRIPTION OF THE DRAWINGS

FIG. 5b is a cross-section of the disposal tape taken along the longitudinal direction in FIG. 5a.

FIG. 7b is an enlarged plan view of the first connection region shown in FIG. 7a.

DETAILED DESCRIPTION OF THE INVENTION

A disposal tape having an extensible portion generally reduces in width with extension and is deformed in part. The deformation can cause the disposal tape to create angle corners that feel hard. Such a hard corner can be a hindrance to the act of wrapping the disposal tape around the diaper. Patent literatures 1 and 2 are silent on that hard feeling corner that can be created upon extending the disposal tape.

The present invention relates to a disposable pull-on diaper free from the above-mentioned disadvantage associated with the conventional techniques.

Figure 1:
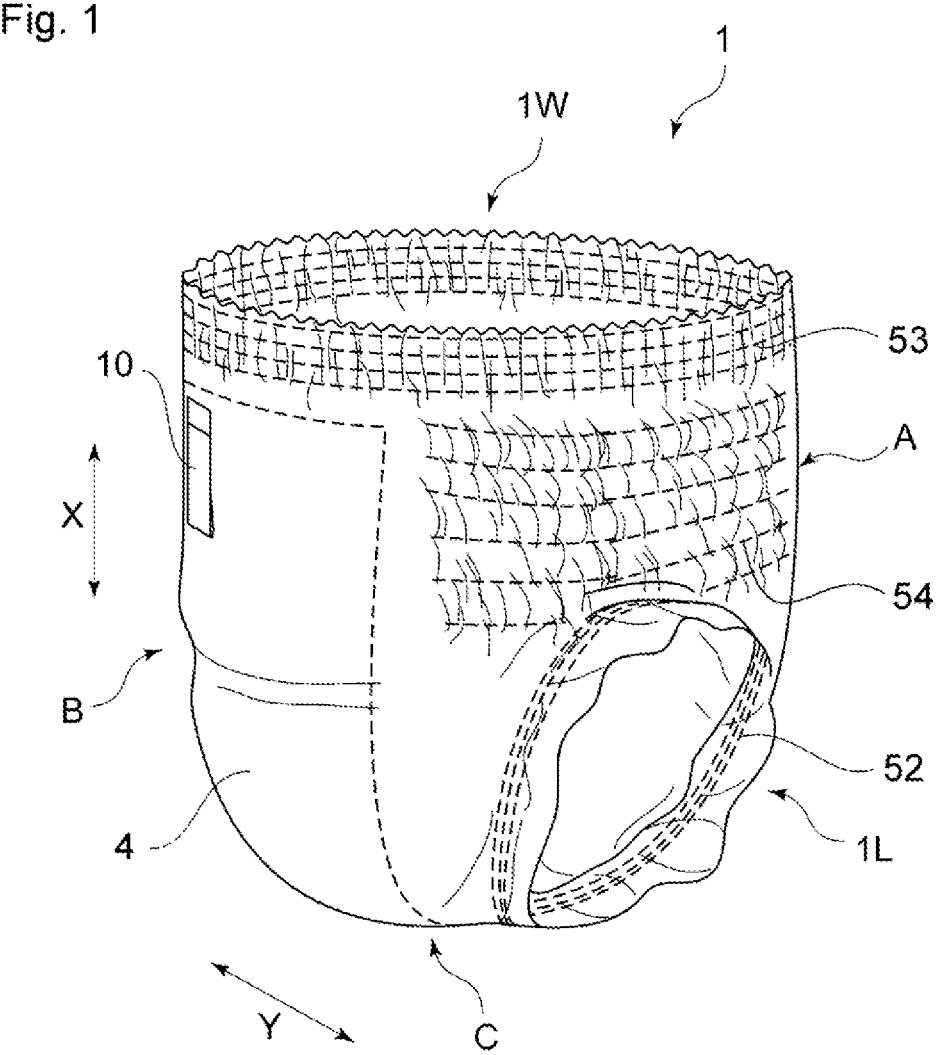
FIG. 1 is a perspective of an embodiment of the disposable pull-on diaper of the present invention.

The present invention will be described on the basis of its preferred embodiment with reference to the accompanying drawings. FIG. 1 illustrates an embodiment of the disposable pull-on diaper according to the present invention. The disposable pull-on diaper 1 illustrated in FIG. 1 (hereinafter, simply "diaper 1") is one type of garments adapted to be worn about the lower torso of a wearer.

As illustrated in FIG. 1, the diaper 1 is of pull-on type having a waist opening 1W which is applied to the wearer's waist and a pair of leg openings 1L and 1L through which the wearer's legs are passed.

The diaper 1 includes an absorbent assembly 4 composed of a topsheet, a backsheet, and an absorbent member 40, and an outer cover 5 disposed on the non-skin facing side of the absorbent assembly 4. The outer cover 5 defines the non-skin facing side, i.e., the outer surface of the diaper 1.

As used herein, the term "skin facing side" refers to the side of the diaper 1 (i.e. an absorbent article) or a member constituting the diaper 1 (e.g., the topsheet 2) that faces the wearer's skin while worn, i.e., the side relatively closer to the wearer's skin. The term "non-skin facing side" refers to the side of the diaper 1 or a member constituting the diaper 1 that faces away from the wearer's skin while worn. As used herein, the expression "while worn" means the state of the diaper 1 applied in the right position to the wearer's body.

The diaper 1 has a front portion A adapted to be worn about the front of a wearer while worn, a crotch portion C adapted to be worn about the crotch of a wearer, and a rear portion B adapted to be worn about the back of a wearer. The front portion A and the rear portion B are joined together along their side edges extending in the longitudinal direction X of the outer cover 5 by a known joining means, such as adhesive bonding, heat sealing, or ultrasonic sealing, so as to form the waist opening 1W and the pair of leg openings 1L and 1L.

Figure 2:
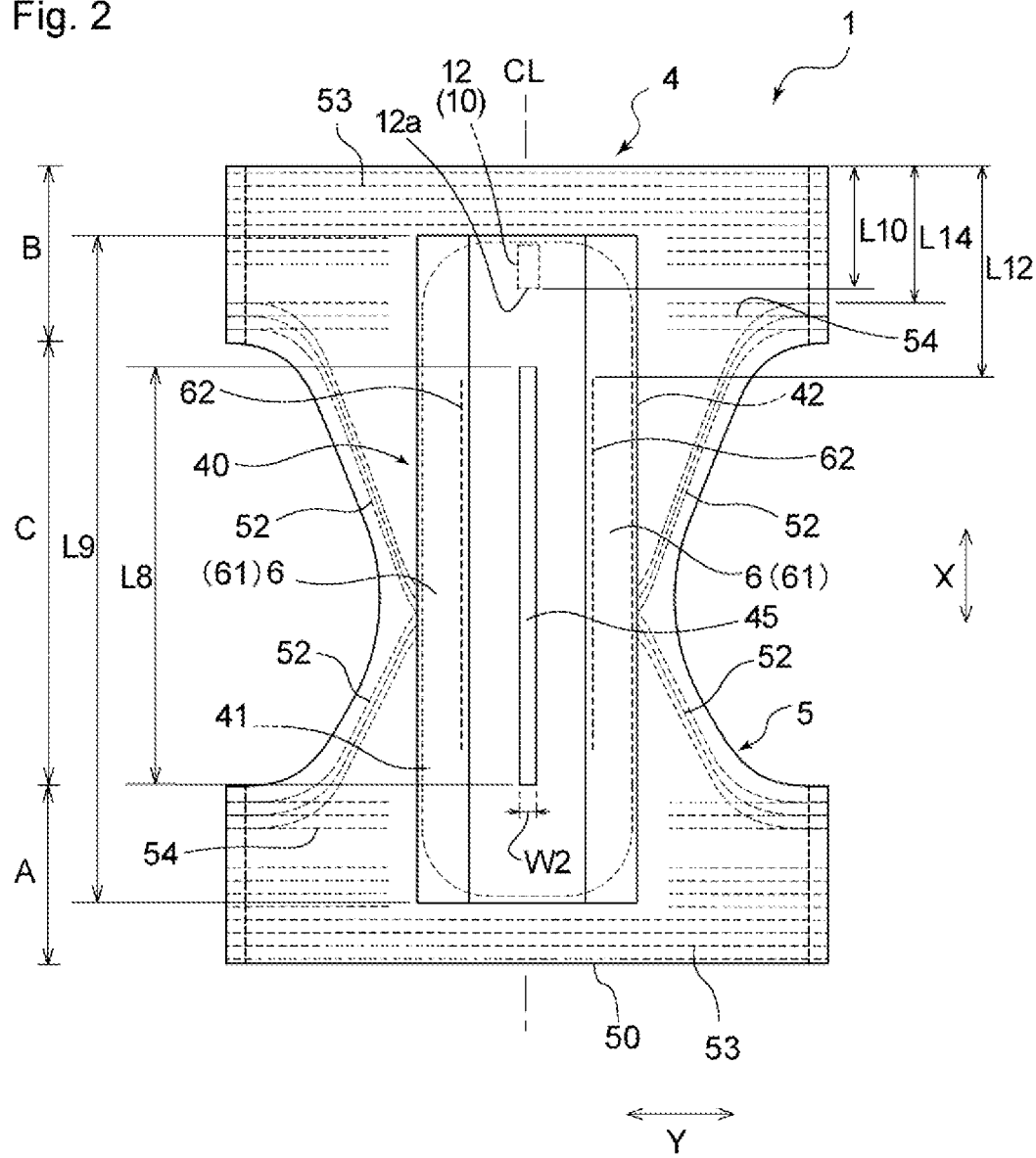
FIG. 2 is a schematic plan of the skin-facing side of the diaper of FIG. 1 in its flat-out, uncontracted state.

FIG. 2 illustrates the diaper 1 in its flat-out, uncontracted state. As used herein, the phrase "flat-out, uncontracted state" of the diaper 1 means a state in which the diaper is opened by tearing the side seams apart and with every elastic member straightened up to the design dimension (the dimension of an article in a flat-out configuration with any influences of elastic members removed).

The diaper 1 has a longitudinal direction X corresponding to the direction from the front portion A to the rear portion B through the crotch portion C and a lateral direction Y that is perpendicular to the longitudinal direction X in a flat-out, uncontracted diaper 1 as shown in FIG. 2. The longitudinal direction X is coincident with the longitudinal direction of the absorbent assembly 4. As shown in FIG. 2, the diaper 1 is symmetric about the longitudinal centerline CL that laterally bisects the diaper 1.

The absorbent assembly 4 includes a topsheet 2 on the skin facing side, a backsheet 3 on the non-skin facing side, and an absorbent member 40 interposed therebetween. All the topsheet 2, backsheet 3, and absorbent member 40 continuously extend in the longitudinal direction X over the whole length of the crotch portion C, straddling the front portion A and the rear portion B. The absorbent member 40 used in the diaper 1 includes a liquid retentive absorbent core 41 and a core wrap sheet 42 wrapping the absorbent core 41. The core wrap sheet is not essential.

As illustrated in FIG. 2, the diaper 1 has a pair of leak proof cuffs 6 and 6 extending in the longitudinal direction X along the opposed longitudinal sides of the absorbent assembly 4. Each leak proof cuff 6 is formed of a water repellent, cuff-forming sheet 61 continuously extending the whole length (in the longitudinal direction X) of the absorbent assembly 4 and at least one cuff elastic member 62 fixed in its stretched state to the cuff-forming sheet 61 along the longitudinally extending proximal edge of the cuff-forming sheet 61. Each cuff 6 is attached to the topsheet via an unshown fixed part extending in the longitudinal direction X. The leak proof cuffs 6 and 6 are raised on the skin facing side by the contraction of the cuff elastic members 62.

The materials used to form the topsheet 2, backsheet 3, and absorbent member 40 that constitute the absorbent assembly 4, the outer cover 5, the leak proof cuffs 6 and 6, and the like may be selected from those commonly used in the art with no particular restriction.

The diaper 1 has, on the rear portion B, a disposal tape 10 as illustrated in FIG. 1. The disposal tape 10 is used to secure the diaper 1 in a configuration for disposal. The disposal tape 10 is located approximately in the lateral middle of the rear portion B. The disposal tape 10 is disposed with its longitudinal direction coincident with the longitudinal direction X of the diaper 1.

Figure 3:
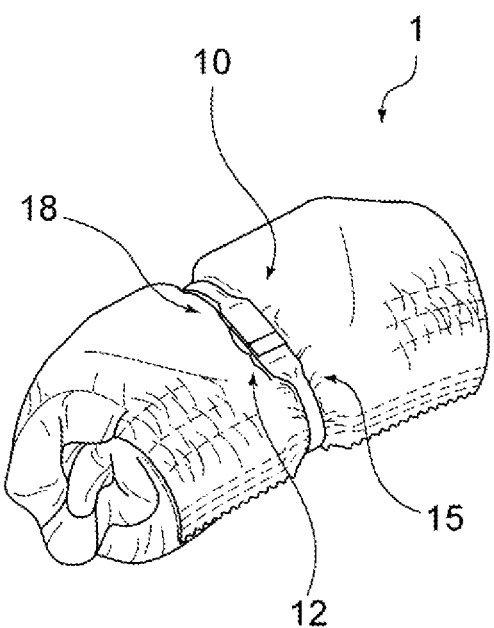
FIG. 3 is a perspective of the diaper of FIG. 1 in a configuration for disposal.

FIG. 3 illustrates the diaper 1 in a configuration for disposal. When the diaper 1 is to be discarded, it is rolled up from the crotch portion C toward the waist opening 1W with the front portion A inside into a rolled-up configuration shown in FIG. 3. The disposal tape 10 on the rear portion B remains exposed on the rolled-up diaper 1. The disposal tape 10 is extended in its longitudinal direction as will be described later and wrapped around the rolled-up diaper 1 to secure the diaper 1 in the rolled-up configuration for disposal.

Figure 4:
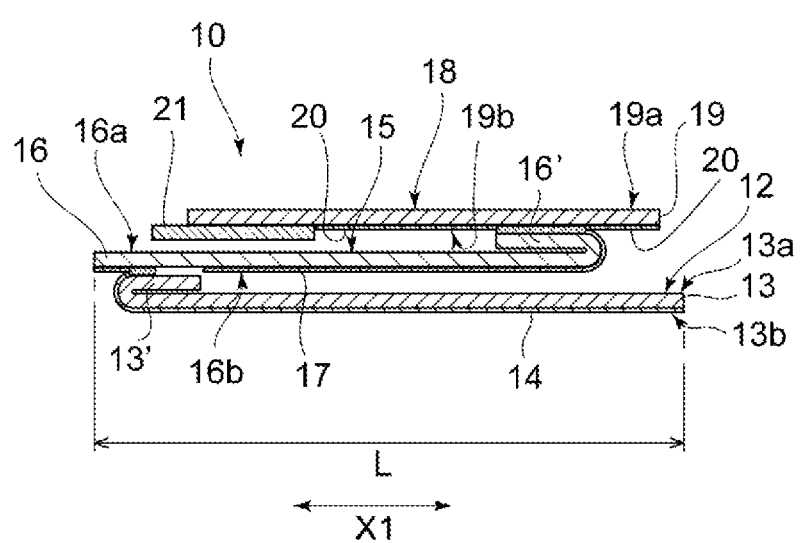
FIG. 4 is a cross-sectional view showing the structure of the disposal tape fixed to the diaper of FIG. 1.

The disposal tape 10 is composed mainly of three portions: a fixed portion 12, an extensible portion 15, and a fastening portion 18. These three portions are arranged in that order in the longitudinal direction X1 of the tape 10 and Z-folded into three panels in that order. FIG. 4 illustrates a cross-sectional structure of the disposal tape 10 in a Z-folded configuration. The fixed portion 12 and the extensible portion 15 are directly connected to each other without any other members therebetween. Similarly, the extensible portion 15 and the fastening portion 18 are directly connected to each other without any other members therebetween.

The fixed portion 12 of the disposal tape 10 has a fixed portion strip 13. The strip 13 has a first side 13a and a second side 13b. The fixed portion strip 13 of the Z-folded disposal tape 10 faces the extensible portion 15 on its first side 13a except for a folded-over portion 13' thereof (hereinafter described), with the second side 13b facing the outer surface of the diaper 1. The fixed portion 12 has an adhesive layer 14 on the second side 13b of the fixed portion strip 13, via which the fixed portion 12 is fixed to the outer surface of the rear portion B of the diaper 1. The disposal tape 10 is fixed to the outer surface of the rear portion B of the diaper 1 via the adhesive layer 14. The fixing of the disposal tape 10 to the outer surface of the diaper 1 can be achieved by a known manner, such as adhesive bonding, e.g., hot-melt adhesive bonding, or fusion bonding.

The extensible portion 15 of the disposal tape 10 is a portion that extends easily with a relatively small tensile force to increase the length of the disposal tape 10 when a pulling force is applied to the disposal tape 10. The extensible portion 15 has an extensible portion strip 16. The strip 16 may have the same or different length and/or the same or different width from those of the strip 13. The strip 16 has a first side 16a and a second side 16b. The strip 16 of the Z-folded disposal tape 10 faces the fastening portion 18 on its first side 16a except for a folded-over portion 16' thereof (hereinafter described), with the second side 16b facing the fixing portion 12. The extensible portion 15 has an adhesive layer 17 on the second side 16b of the strip 16. The adhesive layer 17 releasably attaches the extensible portion 15 to the fixed portion 12 in the Z-folded disposal tape 10. Therefore, the adhesive layer 17 is preferably formed of a pressure-sensitive adhesive having low adhesive strength.

The strip 13 of the fixed portion 12 has a folded-over portion 13' formed by folding one longitudinal end portion thereof toward the extensible portion 15. The folded-over portion 13' is bonded to the second side 16b of one end portion of the strip 16 of the extensible portion 15, whereby the fixed portion 12 and the extensible portion 15 directly connect to each other. The bonding between the fixed portion 12 and the extensible portion 15 can be achieved by a known method, such as adhesive bonding with, e.g., a hot-melt adhesive, or fusion bonding. The extensible portion 15 and the fixed portion 12 are connected in the second connection region 35 hereinafter described.

The fastening portion 18 of the disposal tape 10 is securable at any desired location on the outer surface of the diaper 1 and is adapted to be attached to the outer surface of the diaper 1 to secure the diaper 1 in a disposal configuration. The fastening portion 18 constitutes the leading portion of the disposal tape 10 and has a fastening portion strip 19. The strip 19 may be the same or different in length and/or width with the fixed portion strip 13 or the extensible portion strip 16. The strip 19 has a first side 19a and a second side 19b. The strip 19 of the Z-folded disposal tape 10 faces the extensible portion 15 on its second side 19b. The fastening portion 18 has an adhesive layer 20 provided on the second side 19b of the strip 19. The adhesive layer 20 functions to releasably join the fastening portion 18 and the extensible portion 15 together in the Z-folded disposal tape 10 and also to securely fasten the fastening portion 18 to any part of the outer surface of the diaper 1. The adhesive strength of the adhesive layer 20 is preferably decided with these functions taken into consideration.

The extensible portion strip 16 of the extensible portion 15 has a folded-over portion 16' formed by folding one longitudinal end thereof toward the fastening portion 18. The folded-over portion 16' is bonded to the second side 19b of one end of the fastening portion strip 19 of the fastening portion 18, whereby the extensible portion 15 and the fastening portion 18 directly connect to each other. The bonding between the extensible portion 15 and the fastening portion 18 can be achieved by a known method, such as adhesive bonding with, e.g., a hot-melt adhesive, or fusion bonding. The extensible portion 15 and the fastening portion 18 are connected in the first connection region 34 hereinafter described.

On the other end of the strip 19 of the fastening portion 18 is a pull tab 21 bonded to the second side 19b. The pull tab 21 is formed of a strip separately from the fastening portion strip 19.

The disposal tape 10 composed of the above described three portions is folded in a Z configuration (see FIG. 4). The Z-folded disposal tape 10 is attached to the rear portion B of the diaper 1 with its free end, i.e., the end of the fastening portion 18 having the pull tab 21 attached thereto, pointing toward the waist opening 1W of the diaper 1.

Figure 5A:
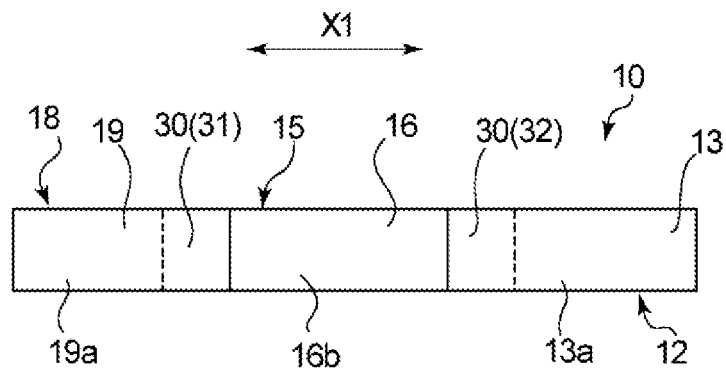
FIG. 5a is a plan schematically illustrating the disposal tape shown in FIG. 1 in its unfolded linear configuration.
Figure 5B:
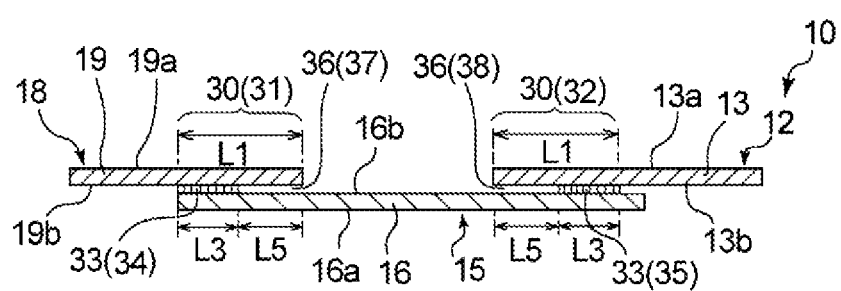

FIGS. 5a and 5b schematically illustrate the disposal tape 10 in an unfolded linear state. As used herein, the expression "unfolded linear" means the state of the disposal tape 10 in which the extensible portion 15 is released from the fixed portion 12, and the fastening portion 18 is released from the extensible portion 15 so that the disposal tape 10 is unfolded into a linear configuration. The expression "unfolded linear" will simply be referred to as "unfolded".

In the unfolded configuration, the disposal tape 10 is composed of the fastening portion 18 connected to one end of the extensible portion 15 and the fixed portion 12 connected to the other end of the extensible portion 15 so that the three portions the fastening portion 18, the extensible portion 15 and the fixed portion 12 are connected in series to form a linear arrangement as illustrated in FIGS. 5a and 5b.

Figure 6:
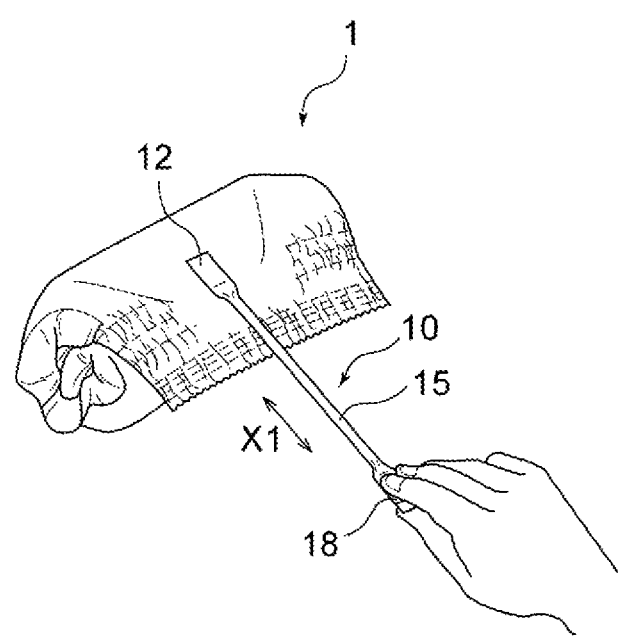
FIG. 6 is a perspective illustration showing the disposal tape of the diaper of FIG. 1 being extended.

The extensible portion 15 in the unfolded configuration is extensible in the longitudinal direction X1 of the disposal tape 10. Unfolded, the extensible portion 15 is manually extensible. Specifically, when a user pinches the fastening portion 18 between, for example, a thumb and an index finger and pulls the disposal tape 10 in the longitudinal direction X1, the extensible portion 15 is extended (see FIG. 6).

As illustrated in FIGS. 5a and 5b, the disposal tape 10 of the present embodiment in the unfolded configuration has a first connection region 31 where the extensible portion 15 and the fastening portion 18 overlap and a second connection region 32 where the extensible portion 15 and the fixed portion 12 overlap. The connection region of the unfolded disposal tape 10 where the extensible portion 15 overlaps an adjacent portion will hereinafter also be referred to as a connection region 30. The adjacent portion is the fastening portion 18 or the fixed portion 12.

In the embodiment, the first connection region 31 includes a first bonded region 34 where the extensible portion 15 and the overlapping fastening portion 18 are bonded to each other, and the second connection region 32 includes a second bonded region 35 where the extensible portion 15 and the overlapping fixed portion 12 are bonded to each other. The bonded region where the extensible portion 15 is bonded to another portion that overlaps the extensible portion 15 will hereinafter also referred to as a bonded region 33. The connection region 30 includes a bonded region 33 where the extensible portion 15 is connected to another portion adjacent thereto in the longitudinal direction X1.

In FIG. 5b, the adhesive layers 20, 17, and 14 for the fastening portion, extensible portion, and fixed portion, respectively, are omitted.

In the unfolded disposal tape 10 of the embodiment, as shown in FIG. 5b, the first connection region 31 includes a first non-bonded region 37 where the extensible portion 15 and the fastening portion 18 are not bonded to each other, and the second connection region 32 includes a second non-bonded region 38 where the extensible portion 15 and the fixed portion 12 are not bonded to each other. The region of the connection region 30 where the extensible portion 15 is not bonded to the adjacent overlapping portion will also be referred to as a non-bonded region 36 (see FIG. 5b).

In the embodiment, as illustrated in FIG. 5b, the first connection region 31 has the first non-bonded region 37 located longitudinally proximal to the first bonded region 34, and the second connection region 32 has the second non-bonded region 38 located longitudinally proximal to the second bonded region 35. Thus, the non-bonded region 36 is located longitudinally proximally to the bonded region 33 in the connection region 30 (see FIG. 5b). The extensible portion 15 and each of the other overlapping portions may be releasably attached to each other in the non-bonded regions 36 unless they are unreleasably bonded to each other.

The second connection region 32 of the embodiment has, in addition to the second non-bonded region 38, another non-bonded region located longitudinally distal to the second bonded region 35 as illustrated in FIG. 5b. In that way, the connection region 30 may have a non-bonded region on longitudinally opposite sides of the bonded region 33 or may have only one non-bonded region located longitudinally proximal to the bonded region 33. In what follows, the term "non-bonded region" refers to the non-bonded region located longitudinally proximal to the bonded region unless otherwise noted.

Figure 7A:
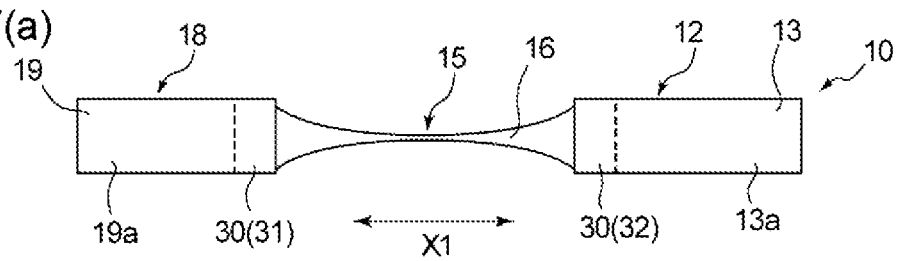
FIG. 7a is a plan schematically illustrating the disposal tape shown in FIG. 5a in an extended state.
Figure 7B:
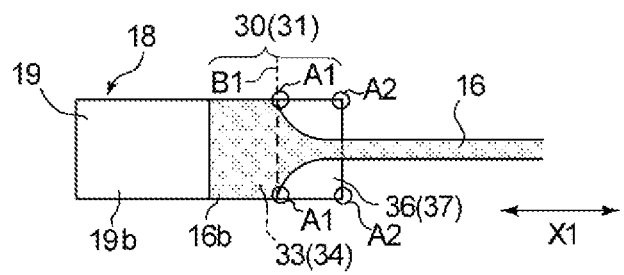

FIG. 7a illustrates the connection regions 30 in an extended state of the disposal tape 10. FIG. 7b illustrates the first connection region 31 in an extended state. On stretching the disposal tape 10 in the longitudinal direction X1, the extensible portion 15 extends and, at the same time, the width of the extensible portion 15 gradually decreases toward the longitudinal center as illustrated in FIG. 7a. However, the extensible portion 15 in the bonded region 33 does not extend because it is bonded to the overlapping fastening portion 18 or fixed portion 12. Therefore, the extensible portion 15 is allowed to extend in the longitudinal direction X1 in the region except the bonded regions 33. In other words, as illustrated in FIG. 7b, the extensible portion 15 extends in the longitudinal direction X1 and undergoes width reduction in the non-bonded regions 36, too, while it neither extends nor reduces in width in the bonded regions 33. When width reduction occurs in the first connection region with the extension of the extensible portion 15, the extensible portion 15 forms an angle at a pair of longitudinally proximal corners A1 of the first bonded region 34 near the boundary B1 with the first non-bonded region 37. On the other hand, the longitudinally proximal, angular corners A2 of the fastening portion 18 overlapping the extensible portion 15 in the first non-bonded region 37 show up according as the width of the extensible portion 15 decreases in the non-bonded region 36. The longitudinally proximal corner of the connection region 30 will be simply called the corner. Similarly, in the second connection region 32, according as the extensible portion 15 extends while decreasing in width, an angle is created at the corners of the second bonded region 35, and the angular corners of the second non-bonded region 38 appear.

As illustrated in FIG. 7b, since the disposal tape 10 has the non-bonded region 36 located longitudinally proximal to the bonded region 33, the corners A1 of the extensible portion 15 created in the bonded region 33 and the corners A2 of the adjacent portion overlapping the extensible portion 15 in the non-bonded region 36 do not align in the thickness direction of the disposal tape 10. The pairs of corners A1 and A2 being out of alignment in the thickness direction, the corners A1 and A2 are prevented from becoming stiff and are less likely to feel hard even with the angles created by, or formed of, these corners. That is, the disposal tape is prevented from forming hard feeling angle corners when extended. As a result, one who takes care of disposal of a used diaper, for example, a caregiver is able to wrap the disposal tape around the diaper smoothly without feeling a pricking pain on one's skin even if the corner formed by extension of the extensible portion 15 comes in contact with one's hand.

Figure 8:
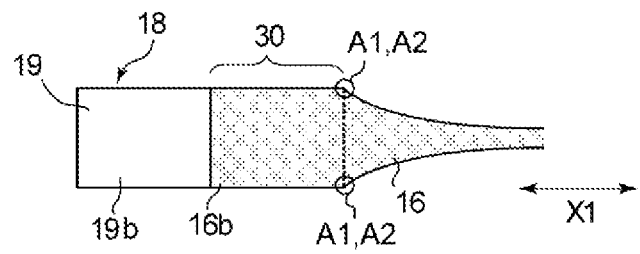
FIG. 8 is a view, which is equivalent to FIG. 7b, of a disposal tape having no non-bonded region.

In contrast, if the extensible portion and an adjacent portion are bonded over the entire area of the connection region, the corners A1 of the extensible portion and the corners A2 of the adjacent portion coincide in the thickness direction of the disposal tape as illustrated in FIG. 8. There are thus formed double corners A1 and A2, which have increased stiffness and feel hard. Such a hard feeling angle corner may come into contact with the caregiver's hand, constituting a hindrance to smooth handling in wrapping the disposal tape around the diaper.

It is only necessary for the disposal tape 10 that at least one of the first connection region 31 and the second connection region 32 have the above discussed bonded region 33 and non-bonded region 36. To facilitate wrapping the disposal tape around the diaper, it is preferred for the first connection region 31 to have the bonded region 33 and non-bonded region 36. It is more preferred for both the first and second connection regions 31 and 32 to have the bonded region 33 and non-bonded region 36.

As described earlier, the non-bonded region 36 of the disposal tape in an unfolded configuration is a region where the extensible portion 15 is not unreleasably bonded to the adjacent portion. The non-bonded region 36 may be formed of a non-coated region where an adhesive capable of unreleasably bonding the extensible portion 15 and the adjacent portion is not applied or a coated region where an adhesive capable of releasably attaching the extensible portion 15 and the adjacent portion to each other is applied.

The disposal tape of the embodiment in the Z-folded configuration has a flap E1 (see FIG. 9a) formed of an end portion of the fastening portion 18 and sticking longitudinally outward from the folded-over portion 16' of the extensible portion 15. The flap E1 corresponds to the first non-bonded region 37 in the unfolded configuration of the disposal tape. More specifically, the second side of the flap E1, which is an end portion of the fastening portion 18, is a coated region coated with an adhesive capable of releasably attaching the fastening portion 18 to the extensible portion 15, namely, the adhesive layer 20. In the Z-folded configuration of the disposal tape of the embodiment, a region 15a (see FIG. 9b) of the region where the folded-over portion 13' of the fixed portion 12 overlaps the extensible portion 15 corresponds to the second non-bonded region 38 of the unfolded disposal tape. More specifically, in the region where the folded-over portion 13' of the fixed portion 12 overlaps the extensible portion 15, the region 15a of the second side 16b of the extensible portion 15 is a non-coated region where no adhesive is applied.

Figure 9A:
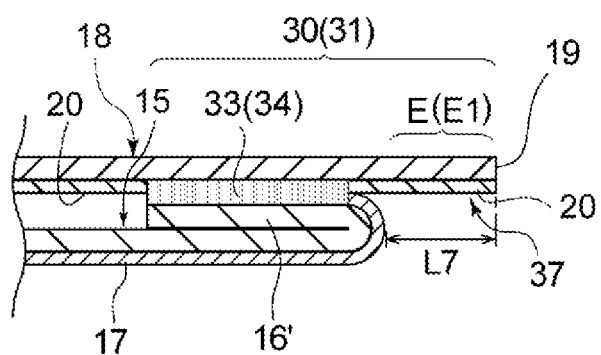
FIG. 9a is an enlarged cross-section of the first connection region shown in FIG. 4.
Figure 9B:
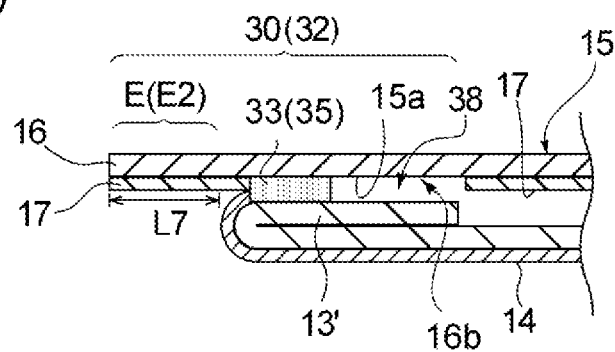
FIG. 9b is an enlarged cross-section of the second connection region shown in FIG. 4.

According to the embodiment, the fastening portion 18 includes the flap E1 that sticks out from the extensible portion 15 in the Z-folded configuration of the disposal tape as illustrated in FIG. 9a. The extensible portion 15 includes a flap E2 that sticks out from the fixed portion in the Z-folded configuration of the disposal tape as illustrated in FIG. 9b. According to this configuration, the flap formed of the fastening portion 18 or the extensible portion 15 that sticks out of the extensible portion 15 or the fixed portion 12, respectively, in the Z-folded configuration of the disposal tape overlaps the extensible portion 15 upon unfolding the disposal tape, thereby to easily provide the corresponding non-bonded region 36. In that way, it is preferred that the first non-bonded region 37 of the first connection region 31 include the flap E1 formed of the fastening portion 18 and sticking out of the extensible portion 15 in the Z-folded configuration of the disposal tape 10. Likewise, it is preferred that the second non-bonded region 38 of the second connection region 32 include the flap E2 formed of the extensible portion 15 and sticks out of the fixed portion 12 in the Z-folded configuration of the disposal tape 10. In the following description, each of the flaps E1 and E2 formed of the fastening portion 18 and the extensible portion 15, respectively, and sticking out of the extensible portion 15 and the fixed portion 12, respectively, will also be referred to as a flap E.

Although the dimensions of the connection regions 30, bonded regions 33, and non-bonded regions 36 are not particularly limited, it is preferred that either one of the first and second connection regions 31 and 32 have the following dimensions. It is more preferred that both of the first and second connection regions 31 and 32 have the following dimensions.

With a view to enhancing the bonding strength between the extensible portion 15 and the overlapping fastening portion 18 or fixed portion 12 in the connection region 30, the non-bonded region 36 preferably has a length L5 (see FIG. 5b) in the longitudinal direction X1 of 5% or more, more preferably 8% or more, preferably 30% or less, more preferably 20% or less, and preferably 5% to 30%, more preferably 8% to 20%, of the length L1 (see FIG. 5b) in the longitudinal direction X1 of the connection region 30. The length L1 of the connection region 30 is the sum of the length of the bonded region 33 in the longitudinal direction X1 and the length of the non-bonded region located proximal to the bonded region 33 in the longitudinal direction X1. Note that the length of another non-bonded region that may be located distal to the bonded region 33 in the longitudinal direction X1 is not included in the length L1.

With a view to more certainly preventing formation of hard feeling corners during extension of the extensible portion 15, the length L5 (see FIG. 5b) of the non-bonded region 36 in the longitudinal direction X1 is preferably 0.4 mm or more, more preferably 0.5 mm or more, preferably 3 mm or less, more preferably 2 mm or less, and preferably 0.4 to 3 mm, more preferably 0.5 to 2 mm.

In the case when the non-bonded region 36 includes a flap E, the flap E preferably has a length L7 (see FIGS. 9a and 9b) in the longitudinal direction X1 of 0.5 mm or more, more preferably 0.7 mm or more, preferably 3 mm or less, more preferably 2 mm or less, and preferably 0.5 to 3 mm, more preferably 0.7 to 2 mm.

With the view to increasing the bonding strength between the extensible portion 15 and the overlapping fastening portion 18 or the fixed portion 12 in the connection region 30 thereby to enhance the strength of the disposal tape 10, the bonded region 33 preferably has a length L3 (see FIG. 5b) in the longitudinal direction X1 of 40% or more, more preferably 50% or more, preferably 85% or less, more preferably 80% or less, and preferably 40% to 85%, more preferably 50% to 80%, of the length L1 (see FIG. 5b) of the connection region 30 in the longitudinal direction X1. With the same view, the length L3 (see FIG. 5b) of the bonded region 33 in the longitudinal direction X1 is preferably 2 mm or more, more preferably 3 mm or more, preferably 5.5 mm or less, more preferably 5 mm or less, and preferably 2 to 5.5 mm, more preferably 3 to 5 mm.

The diaper 1 has a high stiffness region having, in the inside of its thickness direction, the absorbent core 41 and a low stiffness region that is less stiff than the high stiffness region (see FIG. 2). The diaper 1 has waist gathers WG and leg gathers LG in its peripheral region (see FIG. 1). As used herein, the term "peripheral region" denotes the region from each longitudinal end of the absorbent core 41 to the edge of the waist opening. The waist gathers WG and leg gathers LG are often formed in the low stiffness region so as to exhibit good extensibility and contractibility. In the embodiment, the low stiffness region is located in the peripheral region of the diaper 1, and the high stiffness region is located inward of the low stiffness region. The expression "inward of the low stiffness region" as referred to above means "both longitudinally (in the direction X) and laterally (in the direction Y) inward of the low stiffness region".

Figure 10:
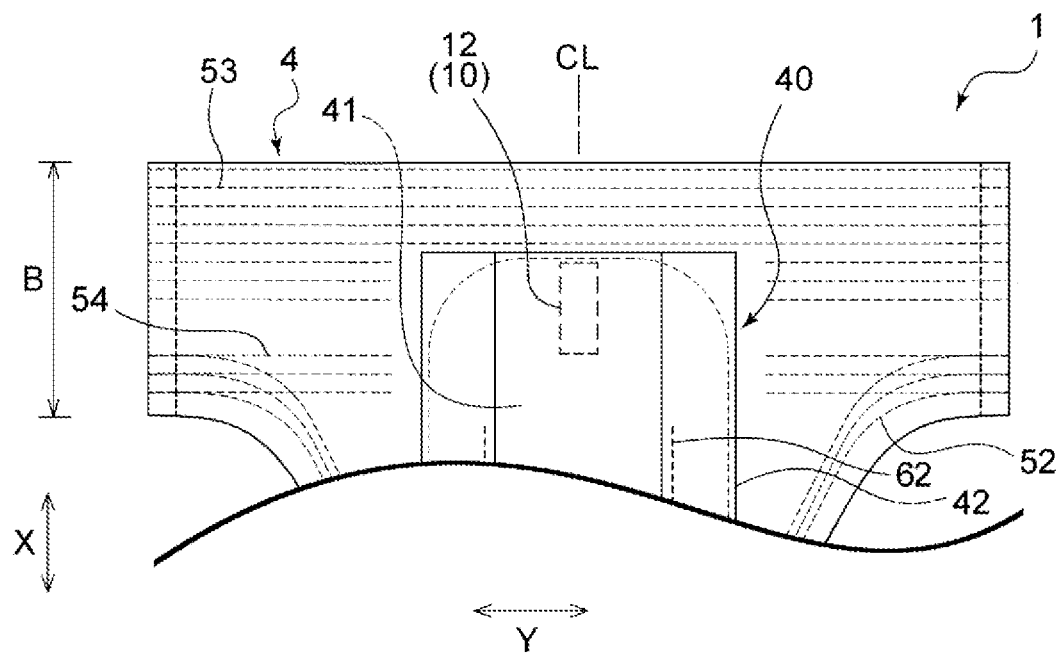
FIG. 10 is a plan showing a location of the disposal tape of the present invention.

It is preferred for at least part of the fixed portion 12 be provided in the high stiffness region so that the disposal tape 10 may be disposed on the high stiffness region when wrapped around the diaper. Being so configured, the disposal tape, when wrapped around the diaper in a rolled-up configuration, is less likely to be curved to raise the corners A1 and A2. For example, the fixed portion 12 may partly overlap the absorbent core 41 in a longitudinally proximal end portion thereof, or, as illustrated in FIG. 10, the fixed portion 12 may entirely be located in the high stiffness region, in which case the fixed portion 12 entirely overlaps the absorbent core 41.

The diaper 1 has a single or a plurality of elastic members 53 and a single or a plurality of elastic members 54 arranged to extend in the lateral direction Y along near the waist opening 1W and in a below-waist portion located between the waist opening 1W and each leg opening 1L. The diaper 1 also has an elastic member 52 arranged along each leg opening 1L. Each elastic member 52 has a portion stretchable in the longitudinal direction X. On contraction, these elastic members achieve a snug fit on a wearer's body to provide wearer comfort and effective prevention of leakage of bodily discharges.

The diaper 1 has an elastic member 62 stretchable in the longitudinal direction X in each leak proof cuff 6 in addition to the above described elastic members. These parts of the diaper 1 stretchable and contractible in a predetermined direction, such as the longitudinal direction X or the lateral direction Y, by the action of the elastic members will be each called to as an elasticized portion.

The outer surface of the diaper 1 may have unevenness ascribed to the contraction of the elasticized portion. When the disposal tape is attached to such an uneven surface of the diaper 1, it can come off unintentionally. With a view to securely fixing the disposal tape 10 to the outer surface of the diaper 1, the fixed portion 12 is preferably attached at a location that does not overlap the elasticized portion in a plan view of the diaper 1. FIG. 2 illustrates an example of such a preferred location, in which the longitudinally proximal end 12a of the fixed portion 12 is located closer, than the longitudinally stretchable elasticized portions, to the waist edge 50 defining the waist opening 1W. In this case, the proximal end 12a of the fixed portion 12 is located closer, to the waist edge 50 of the waist opening 1W in the rear portion B, than either of the rear end of each cuff elastic member 62 and the rear end of each elastic member 52 disposed along the leg opening. More specifically, the distance L10 from the waist edge 50 in the rear portion B to the proximal end 12a of the fixed portion 12 is shorter than either of the distance L12 to the cuff elastic members 62 and the distance L14 to the leg elastic members 52 (see FIG. 2).

In order to maintain the secure attachment of the disposal tape 10 to the outer surface of the diaper 1, the ratio of L12 (the distance from the rear waist edge 50 to the cuff elastic members 62, see FIG. 2) to L10 (the distance from the rear waist edge 50 to the proximal end 12a of the fixed portion 12, see FIG. 2), L12/L10, is preferably 1.05 or greater, more preferably 1.1 or greater, preferably 2.0 or smaller, more preferably 1.75 or smaller, and preferably 1.05 to 2.0, more preferably 1.1 to 1.75.

For the same purpose, the ratio of L14 (the distance from the waist edge 50 to the leg elastic member 52, see FIG. 2) to L10, L14/L10, is preferably 1.1 or greater, more preferably 1.2 or greater, preferably 2.5 or smaller, more preferably 2.2 or smaller, and preferably 1.1 to 2.5, more preferably 1.2 to 2.2.

In order for the fastening portion 18 or the fixed portion 12 to have moderate strength and yet feel soft at the corners A2, which show up with the extension of the extensible portion 15, either one or both of the fastening portion 18 and the fixed portion 12 is preferably made of a material at a basis weight of 50 g/m² or more, more preferably 60 g/m² or more, preferably 90 g/m² or less, more preferably 80 g/m² or less, and preferably 50 to 90 g/m², more preferably 60 to 80 g/m². In particular, the basis weight of the material forming the fastening portion 18 is preferably in the above range. It is more preferred that both the basis weight of the material forming the fastening portion 18 and the basis weight of the material forming the fixed portion 12 be in the above range.

With the view to preventing formation of angular corners A2, it is preferred for either one or both of the fastening portion 18 and the fixed portion 12 to have its or their proximal end corners rounded off. Specifically, the corners of the fastening portion 18 in the first non-bonded region 37 and/or the corners of the fixed portion 12 in the second non-bonded region 38 are preferably rounded off.

In order for the disposal tape 10 to be provided compactly on the outer surface of a diaper while providing an extended length enough to wrap around the diaper, the overall length L (see FIG. 4) of the disposal tape 10 in the Z-fold configuration is preferably 30 mm or longer, more preferably 35 mm or longer, preferably 50 mm or shorter, more preferably 45 mm or shorter, and preferably 30 to 50 mm, more preferably 35 to 45 mm. The overall length L (FIG. 4) of the disposal tape 10 in the Z-fold configuration is the maximum length of the tape in the Z-fold configuration.

With the view to providing the sufficient extended length for wrapping around a diaper, the extensible portion 15 is preferably extensible to 150 mm or longer, more preferably 180 mm or longer, even more preferably 200 mm or longer. As used herein, the term "extended length" refers to the length inclusive of the bonded regions 33 of both ends of the extensible portion 15.

To facilitate wrapping around the diaper, the maximum extended length of the extensible portion 15 is preferably 150 mm or longer, more preferably 180 mm or longer, preferably 250 mm or shorter, more preferably 240 mm or shorter, and preferably 150 to 250 mm, more preferably 180 to 240 mm.

As used herein, the term "maximum extended length" of the extensible portion 15 refers to the maximum length of the extensible portion 15 extended until breakage. The maximum extended length can be measured by the method below.

A Z-folded disposal tape is unfolded by peeling the extensible portion from the fixed portion. The extensible portion is clamped at both longitudinal ends, i.e., in the bonded regions thereof in a tensile tester (e.g., AUTOGRAPH AG-X, from Shimadzu Corp.) with the longitudinal direction of the tape coincident with the loading direction. The clamped extensible portion is pulled at a jaw separation rate of 300 mm/min to record the tensile strength varying with the increase in jaw separation. The sum of the increase in jaw separation at which the tensile strength reaches the maximum and the length of the extensible portion before extension is defined to be the maximum extended length of the extensible portion 15.

With the view to preventing formation of hard angle corners in the connection region 30 after extension, the disposal tape 10 is preferably capable of securing the diaper 1 in a disposal configuration with the fixed portion 12 located in the high stiffness region. In that case, a user is able to wrap the disposal tape 10 with the extensible portion 15 extended around the absorbent core 41 to secure the diaper 1 in a disposal configuration. That is, the disposal tape 10 is wrapped around the outer side of the rolled-up absorbent core 41 in a disposal configuration.

As illustrated in FIG. 2, the absorbent core 41 of the embodiment has a slit extending in the longitudinal direction in the transverse middle thereof. The slit constitutes a low basis weight region 45. As used herein, the term "low basis weight region" denotes a region in which the material forming the absorbent core 41 has a basis weight of not more than 50 g/m$^2$. The term "low basis weight region" includes a fiber-free region where an absorbent core-forming material is absent. The low basis weight region is exemplified by a slit cut through the entire thickness of the absorbent core 41.

When the diaper 1 of the embodiment is rolled up into a disposal configuration, a groove is formed on the outer side of the diaper 1 along the slit of the absorbent core 41. With a view to fitting the disposal tape 10 in the groove in wrapping around the diaper so as to stably secure the diaper in the disposal configuration, the fixed portion 12 of the disposal tape 10 is preferably disposed on the longitudinal extension from the low basis weight region 45.

To enhance the above effect, the width W1 of the disposal tape 10 is preferably equal to or smaller than the width W2 of the low basis weight region 45, more preferably smaller than the width W2. For the disposal tape 10 to fit in the groove easily, the width W1 of the disposal tape 10 is preferably 20% to 100%, more preferably 30% to 80%, of the width W2 of the low basis weight region 45.

In order for the low basis weight region to form the groove easily on the outer side of the rolled-up diaper 1, the low basis weight region 45 preferably has a length L8 (see FIG. 2) in the longitudinal direction X of 30% to 80%, more preferably 40% to 60%, of the length 9 (see FIG. 2) of the absorbent core 41 in the longitudinal direction X.

To facilitate extending the disposal tape 10 and yet prevent unintentional extension, the tensile strength Pa at which the extensible portion 15 starts extending is preferably 1.0 N or greater, more preferably 3 N or greater, preferably 12 N or smaller, more preferably 6.5 N or smaller, and preferably 1.0 to 12 N, more preferably 3 to 6.5 N.

The tensile strength (N) at which the extensible portion starts extending is measured by the same method as the above described method for measuring the maximum extended length of the extensible portion 15, except that the tensile tester jaws are clamped to the non-bonded regions of the extensible portion at an initial jaw spacing of 10 mm. The strength at the first local maximum point presented in the tensile strength curve as measured by that method is taken as the tensile strength (N) at which the extensible portion starts extending. The first local maximum point is the local maximum point that appears first in the recorded curve of the tensile strength (N) varying with the increase of jaw separation. When a first local maximum point is not clearly distinguished or not observed, the maximum load within a range of from 30% to 70% of the maximum elongation is regarded as the strength at the first local maximum point. The maximum of the tensile strength varying with the increase in jaw separation is taken as breaking strength, and the point at which the breaking strength is presented is taken "at break". The elongation at break is taken as 100% (the maximum elongation).

In order for the extensible portion 15 to be extensible, it is necessary to select an appropriate material as the strip 16 that makes the extensible portion 15. For example, extensible films may be used as the strip 16. The extensible film may be a single or multi-layered film, such as a co-extruded film. Preferred materials for making extensible films include polyolefins, such as linear low-density polyethylene. At least one member selected from the group consisting of polyvinyl chloride, ethylene-vinyl acetate copolymers, and polyvinyl alcohol is also preferred. It is also advantageous to use a material having a permanent deformation of at least 50%, more preferably at least 70%.

The strip 13 or 19 that constitutes the fixed portion 12 or the fastening portion 18, respectively, may be of the same material of the strip 16 or any conventionally used inextensible, i.e., plastically undeformable materials, including sheets or films made of resins, nonwoven fabrics, and woven fabrics. Even when the strip 13 for the fixed portion is formed of an extensible material, the extensibility does not develop in the part of the strip 13 that is fixed to the outer surface of the diaper 1.

The adhesive layer 17 by which the extensible portion 15 is releasably attached to the fixed portion 12 and the adhesive layer 20 by which the fastening portion 18 is releasably attached to the extensible portion 15 are usually formed of a rubber pressure-sensitive adhesive or an acrylic pressure-sensitive adhesive, with the rubber pressure-sensitive adhesive being preferred. Examples of suitable rubber pressure-sensitive adhesives include synthetic rubbers, such as styrene-butadiene block copolymers and hydrogenated styrene-butadiene block copolymers; and blends of the synthetic rubbers and resins. A heat-seal, and a hot-melt pressure-sensitive adhesive, or melt-blown or otherwise fiberized adhesive or pressure-sensitive adhesive may also be used.

The adhesive layer 17 for the extensible portion may be provided all over the second side 16b, except the non-bonded regions 36, of the extensible portion strip 16. The adhesive layer 20 for the fastening portion may be provided all over the second side 19b, except the non-bonded region 36, of the fastening portion strip 19. Alternatively, the adhesive layers 17 and 20 may be provided discontinuously by discontinuously applying the pressure-sensitive adhesive.

The disposal tape 10 to be provided on the outer surface of the diaper 1 is made by overlapping one end portion of the fastening portion strip 19 with one end portion of the extensible portion strip 16, overlapping one end portion of the fixed portion strip 13 with the other end portion of the strip 16, and bonding the overlapped end portions using a known method, such as adhesive bonding, to connect the three strips together using a known method such as adhesive bonding. In order to form the flaps E1 and E2, the fastening portion strip 19 may be bonded to a region longitudinally spaced inward of one end edge of the extensible portion strip 16, and the fixed portion strip 13 may be bonded to a region longitudinally spaced inward of the other end edge of the extensible portion strip 16. A part of the strip may be folded over itself along the bonded region to form a folded-over portion as in the above-mentioned embodiment.

While the present invention has been described on the basis of its preferred embodiment, it should be understood that the present invention is not limited thereto. For instance, while in the above embodiment the disposal tape 10 is provided on the rear portion B of the diaper 1, the location of the disposal tape 10 is not limited thereto and may be in the front portion A or the crotch portion C.

While in the above embodiment the disposal tape 10 is disposed in the lateral middle of the diaper 1, the location of the disposal tape 10 is not limited thereto and may be in either the left or the right half of the diaper 1. While in the above embodiment the disposal tape 10 is attached with its longitudinal direction X1 coincident with the longitudinal direction X of the diaper 1, the direction of attachment is not limited thereto. For example, the disposal tape 10 may be attached with its longitudinal direction X1 coincident with the lateral direction Y of the diaper 1.

While in the above embodiment a pull tab 21 is attached to the free end of the fastening portion strip 19, the disposal tape 10 does not always need to have the pull tab 21.

The pull-on garment according to the present invention is not limited to a pull-on diaper for children or adults and may be a panty type sanitary napkin and the like.

In relation to the foregoing embodiments of the present invention, the following additional disposable pull-on diapers are also disclosed.

<1> A disposable pull-on diaper having a waist opening and a pair of leg openings and comprising a front portion adapted to be worn about the front of a wearer, a crotch portion adapted to be worn about the crotch of a wearer, and a rear portion adapted to be worn about the back of a wearer, the diaper further comprising a disposal tape on the outer surface thereof, the disposal tape comprising a fixed portion fixed to the outer surface of the diaper, an extensible portion, and a fastening portion arranged and Z-folded in that order along the longitudinal direction of the disposal tape, the fastening portion and the extensible portion in the Z-folded disposal tape being releasably attached to each other, the extensible portion and the fixed portion in the Z-folded disposal tape being releasably attached to each other, the extensible portion being extensible in the longitudinal direction of the disposal tape in an unfolded configuration of the disposal tape, the disposal tape in the unfolded configuration having a first connection region where the extensible portion and the fastening portion overlap and a second connection region where the extensible portion and the fixed portion overlap, at least one of the first connection region and the second connection region having a bonded region where the extensible portion and the overlapping fastening portion or fixed portion are bonded to each other and a non-bonded region where the extensible portion and the overlapping fastening portion or fixed portion are not bonded to each other, the non-bonded region being located longitudinally proximal to the bonded region.

<2> The disposable pull-on diaper as set forth in clause <1>, wherein the extensible portion has an adhesive layer on its side facing the fixed portion, the adhesive layer releasably attaching the extensible portion to the fixed portion in the Z-folded disposal tape.

<3> The disposal pull-on diaper as set forth in clause <1> or <2>, wherein the non-bonded region is formed of a non-coated region where an adhesive capable of unreleasably bonding the extensible portion and the fastening portion or fixed portion is absent or a coated region where an adhesive capable of releasably attaching the extensible portion and the fastening portion or fixed portion to each other is applied.

<4> The disposal pull-on diaper as set forth in clause <1> or <2>, wherein the non-bonded region is a coated region where an adhesive capable of releasably attaching the extensible portion and the fastening portion or fixed portion to each other is applied.

<5> The disposal pull-on diaper as set forth in any one of clauses <1> to <4>, wherein the non-bonded region has a length L5 in the longitudinal direction of 5% or more, preferably 8% or more, further 30% or less, preferably 20% or less of a length L1 in the longitudinal direction of the first or second connection region.

<6> The disposal pull-on diaper as set forth in any one of clauses <1> to <5>, wherein the non-bonded region has a length L5 in the longitudinal direction of 0.4 mm or more, preferably 0.5 mm or more, further 3 mm or less, preferably 2 mm or less.

<7> The disposal pull-on diaper as set forth in any one of clauses <1> to <6>, wherein the bonded region has a length L3 in the longitudinal direction of 40% or more, preferably 50% or more, further 85% or less, preferably 80% or less of a length L1 in the longitudinal direction of the first or second connection region.

<8> The disposal pull-on diaper as set forth in any one of clauses <1> to <7>, wherein the bonded region has a length L3 in the longitudinal direction of 2 mm or more, preferably 3 mm or more, further 5.5 mm or less, preferably 5 mm or less.

<9> The disposal pull-on diaper as set forth in any one of clauses <1> to <8>, wherein the non-bonded region of the first connection region comprises a part of the fastening portion sticking out of the extensible portion in the Z-folded configuration of the disposal tape.

<10> The disposal pull-on diaper as set forth in clause <9>, wherein the part of the fastening portion sticking out of the extensible portion has a length of 0.5 mm or more.

<11> The disposable pull-on diaper as set forth in any one of clauses <1> to <10>, wherein the non-bonded region of the first connection region comprises a part of the fastening portion sticking out of the extensible portion in the Z-folded configuration of the disposal tape, the part having a length L7 of 0.5 mm or more, preferably 0.7 mm or more, further 3 mm or less, more preferably 2 mm or less in the longitudinal direction.

<12> The disposal pull-on diaper as set forth in any one of clauses <1> to <11>, wherein the diaper has a low stiffness region in a peripheral region thereof and a high stiffness region inward of the low stiffness region, and at least part of the fixed portion is located in the high stiffness region.

<13> The disposable pull-on diaper as set forth in clause <12>, further comprising an absorbent core, wherein the high stiffness region has the absorbent core in its thickness direction.

<14> The disposable pull-on diaper as set forth in clause <13>, wherein the fixed portion entirely overlaps the absorbent core.

<15> The disposable pull-on diaper as set forth in any one of clauses <1> to <14>, having a longitudinal direction corresponding to the direction from the front portion to the rear portion through the crotch portion and a lateral direction perpendicular to the longitudinal direction and having an elasticized portion extensible and contractible in the longitudinal direction,
wherein the disposal tape is in the rear portion with the proximal end of the fixed portion being located closer than the elasticized portion to an edge of the waist opening.

<16> The disposable pull-on diaper as set forth in any one of clauses <1> to <15>, having a longitudinal direction corresponding to the direction from the front portion to the rear portion through the crotch portion and a lateral direction perpendicular to the longitudinal direction and
comprising an absorbent assembly comprising a topsheet on a skin facing side, a backsheet on a non-skin facing side, and an absorbent member between the topsheet and the backsheet and a pair of leak proof cuffs along opposed sides of the absorbent assembly extending in the longitudinal direction,
the leak proof cuffs each comprising a cuff-forming sheet and at least one cuff elastic member fixed in a stretched state in the longitudinal direction, and
a ratio of a distance L12 from an edge of the waist opening of the rear portion to the cuff elastic member to a distance L10 from the edge of the waist opening of the rear portion to the proximal end of the fixed portion, L12/L10, being 1.05 or greater, preferably 1.1 or greater, further 2.0 or smaller, preferably 1.75 or smaller.

<17> The disposable pull-on diaper as set forth in clause <16>, wherein a ratio of a distance L14 from the edge of the waist opening to a leg elastic member fixed along the leg opening to the distance L10, L14/L10, is 1.1 or greater, preferably 1.2 or greater, further 2.5 or smaller, more preferably 2.2 or smaller.

<18> The disposable pull-on diaper as set forth in any one of clauses <1> to <17>, wherein at least one of the fastening portion and the fixed portion is made of a material having a basis weight of 90 g/m$^2$ or less.

<19> The disposable pull-on diaper as set forth in any one of clauses <1> to <18>, wherein at least one of the fastening portion and the fixed portion is made of a material having a basis weight of 50 g/m$^2$ or more, preferably 60 g/m$^2$ or more, further 90 g/m$^2$ or less, preferably 80 g/m$^2$ or less.

<20> The disposable pull-on diaper as set forth in any one of clauses 1 to 19, wherein at least one of the fastening portion and the fixed portion has a longitudinally proximal end corner in the non-bonded region thereof, the longitudinally proximal end corner being rounded off <21> The disposable pull-on diaper as set forth in any one of clauses <1> to <20>, wherein the fastening portion has an end corner in the non-bonded region of the first connection region, and the fixed portion has an end corner in the non-bonded region of the second connection region, both the end corner of the fastening portion and the end corner of the fixed portion being rounded off.

<22> The disposable pull-on diaper as set forth in any one of clauses <1> to <21>, wherein the disposal tape in the Z-folded configuration has an overall length of 50 mm or shorter.

<23> The disposable pull-on diaper as set forth in any one of clauses <1> to <22>, wherein the disposal tape in the Z-folded configuration has an overall length L of 30 mm or longer, preferably 35 mm or longer, further 50 mm or shorter, preferably 45 mm or shorter.

<24> The disposable pull-on diaper as set forth in any one of clauses <1> to <23>, wherein the extensible portion is extensible to a maximum extended length of 150 mm or longer, more preferably 180 mm or longer, 250 mm or shorter, more preferably 240 mm or shorter.

<25> The disposal pull-on diaper as set forth in any one of clauses <1> to <24>, wherein the diaper has a low stiffness region in a peripheral region thereof and a high stiffness region inward of the low stiffness region, the extensible portion is extensible to 150 mm or longer, and the disposal tape is capable of securing the diaper in a configuration for disposal with the fixed portion being located in the high stiffness region.

<26> The disposable pull-on diaper as set forth in any one of clauses <1> to <25>, further comprising an absorbent core and having a longitudinal direction corresponding to the direction from the front portion to the rear portion through the crotch portion and a lateral direction perpendicular to the longitudinal direction, the absorbent core having a low basis weight region extending in the longitudinal direction in the transverse middle thereof, and the disposal tape being disposed on a longitudinal extension from the low basis weight region.

<27> The disposable pull-on diaper as set forth in clause <26>, wherein the disposal tape has a width equal to or smaller than that of the low basis weight region.

<28> The disposable pull-on diaper as set forth in clause <26> or <27>, wherein the disposal tape has a width W1 of 20% to 100%, preferably 30% to 80%, of the width W2 of the low basis weight region.

<29> The disposable pull-on diaper as set forth in any one of clauses <26> to <28>, wherein the low basis weight region has a length L8 in the longitudinal direction of 30% to 80%, preferably 40% to 60% of the length L9 of the absorbent core in the longitudinal direction.

<30> The disposable pull-on diaper as set forth in any one of clauses <1> to <29>, wherein the extensible portion is designed to start extending at a tensile strength of 1.0N or greater, preferably 3N or greater, further 12 N or smaller, preferably 6.5 N or smaller.

INDUSTRIAL APPLICABILITY

The disposal tape according to the present invention is prevented from forming hard feeling angle corners on being extended.

The invention claimed is:

1. A disposable pull-on diaper having a waist opening and a pair of leg openings and comprising a front portion adapted to be worn about the front of a wearer, a crotch portion adapted to be worn about the crotch of a wearer, and a rear portion adapted to be worn about the back of a wearer,
the diaper further comprising a disposal tape on the outer surface thereof,
the disposal tape comprising a fixed portion fixed to the outer surface of the diaper, an extensible portion, and a fastening portion arranged and Z-folded in that order along the longitudinal direction of the disposal tape,
the fastening portion and the extensible portion in the Z-folded disposal tape being releasably attached to each other,
the extensible portion and the fixed portion in the Z-folded disposal tape being releasably attached to each other,
the extensible portion being extensible in the longitudinal direction of the disposal tape in an unfolded configuration of the disposal tape,
the disposal tape in the unfolded configuration having a first connection region where the extensible portion and the fastening portion overlap and a second connection region where the extensible portion and the fixed portion overlap, at least one of the first connection region and the second connection region having a bonded region where the extensible portion and the overlapping fastening portion or fixed portion are bonded to each other and a non-bonded region where the extensible portion and the overlapping fastening portion or fixed portion are not bonded to each other, the non-bonded region being located longitudinally proximal to the bonded region,
wherein at least one of the fastening portion and the fixed portion has a longitudinally proximal end corner in the non-bonded region thereof, the longitudinally proximal end corner being rounded off.

2. The disposable pull-on diaper according to claim 1, wherein the extensible portion has an adhesive layer on its side facing the fixed portion, the adhesive layer releasably attaching the extensible portion to the fixed portion in the Z-folded disposal tape.

3. The disposal pull-on diaper according to claim 1, wherein the non-bonded region is formed of a non-coated region where an adhesive capable of unreleasably bonding the extensible portion and the fastening portion or fixed portion is absent or a coated region where an adhesive capable of releasably attaching the extensible portion and the fastening portion or fixed portion to each other is applied.

4. The disposal pull-on diaper according to claim 1, wherein the non-bonded region is a coated region where an adhesive capable of releasably attaching the extensible portion and the fastening portion or fixed portion to each other is applied.

5. The disposal pull-on diaper according to claim 4, wherein the non-bonded region of the first connection region comprises a part of the fastening portion sticking out of the extensible portion in the Z-folded configuration of the disposal tape.

6. The disposal pull-on diaper according to claim 1, wherein the diaper has a low stiffness region in a peripheral region thereof and a high stiffness region inward of the low stiffness region, and at least part of the fixed portion is located in the high stiffness region.

7. The disposable pull-on diaper according to claim 6, further comprising an absorbent core, wherein the high stiffness region has the absorbent core in its thickness direction.

8. The disposal pull-on diaper according to claim 7, wherein the fixed portion entirely overlaps the absorbent core.

9. The disposable pull-on diaper according to claim 1, wherein at least one of the fastening portion and the fixed portion is made of a material having a basis weight of 50 to 90 g/m$^2$.

10. The disposable pull-on diaper according to claim 1, wherein the fastening portion has an end corner in the non-bonded region of the first connection region, and the fixed portion has an end corner in the non-bonded region of the second connection region, both the end corner of the fastening portion and the end corner of the fixed portion being rounded off.

11. The disposal pull-on diaper according to claim 1, wherein the diaper has a low stiffness region in a peripheral region thereof and a high stiffness region inward of the low stiffness region, the extensible portion is extensible to 150 mm or longer, and the disposal tape is capable of securing the diaper in a configuration for disposal with the fixed portion being located in the high stiffness region.

12. The disposable pull-on diaper according to claim 1, further comprising an absorbent core and having a longitudinal direction corresponding to the direction from the front portion to the rear portion through the crotch portion and a lateral direction perpendicular to the longitudinal direction, the absorbent core having a low basis weight region extending in the longitudinal direction in the transverse middle thereof, and the disposal tape being disposed on a longitudinal extension from the low basis weight region.

13. The disposable pull-on diaper according to claim 12, wherein the disposal tape has a width W1 equal to or smaller than the width W2 of the low basis weight region.

14. The disposable pull-on diaper according to claim 1, wherein the extensible portion is designed to start extending at a tensile strength of 1.0 to 12 N.

* * * * *